United States Patent
Chan

(10) Patent No.: US 6,916,922 B2
(45) Date of Patent: Jul. 12, 2005

(54) PROCESS FOR THE PREPARATION OF 1,2,3,4,8,9,10,10A-OCTAHYDRO-7BH-CYCLOPENTA [B] [1,4] DIAZEPINO- [6,7,1-HI] INDOLE DERIVATIVES

(75) Inventor: Anita W-Y. Chan, Fort Lee, NJ (US)

(73) Assignee: Wyeth, Madison, NJ (US)

( * ) Notice: Subject to any disclaimer, the term of this patent is extended or adjusted under 35 U.S.C. 154(b) by 220 days.

(21) Appl. No.: 10/016,229

(22) Filed: Nov. 2, 2001

(65) Prior Publication Data

US 2002/0055504 A1 May 9, 2002

Related U.S. Application Data

(60) Provisional application No. 60/245,591, filed on Nov. 3, 2000.

(51) Int. Cl.$^7$ ............................................. C07D 243/00
(52) U.S. Cl. ........................................ 540/555; 540/556
(58) Field of Search .................................. 540/555, 556

(56) References Cited

U.S. PATENT DOCUMENTS

| | | | |
|---|---|---|---|
| 3,914,250 A | 10/1975 | Kim | 260/315 |
| 2002/0055630 A1 | 5/2002 | Weimaker et al. | 540/556 |
| 2002/0058689 A1 | 5/2002 | Weimaker et al. | 514/411 |
| 2002/0062022 A1 | 5/2002 | Sabb et al. | 540/556 |
| 2002/0086860 A1 | 7/2002 | Sabb et al. | 514/220 |
| 2002/0107242 A1 | 8/2002 | Sabb et al. | 514/219 |
| 2002/0119966 A1 | 8/2002 | Sabb et al. | 514/219 |
| 2002/0128261 A1 | 9/2002 | Sabb et al. | 514/219 |

FOREIGN PATENT DOCUMENTS

| | | |
|---|---|---|
| WO | WO 96/29316 | 9/1996 |
| WO | WO 00/35922 | 6/2000 |
| WO | WO 02/08186 | 1/2002 |

OTHER PUBLICATIONS

H.P. Haerter et al., Chimia, 30, 50–52, (1976).
D. Kim, J. Heterocyclic Chem., 13, 1187–1192 (1976).
S. Archer et al., J. Am. Chem. Soc., 79, 5783–5785 (1957).
L. Zhang et al., Tetrahedron Letters, 36(46), 8387–8390 (1995).
G.E. Stokker, Tetrahedron Letters, 37(31), 5453–5456 (1996).
Cuadro et al., Synthetic Communications, 21(4), 535–544 (1991).
W. Perkin et al., J. Chem. Soc., 123, 3242–3247 (1923).
H. Booth et al., J. Chem. Soc., 158, 2302–2311 (1958).
Gregory E. Martin et al., J. Med. Chem., 1989, 1052–1056, 32.
J.L. Browning et al., Society for Neuroscience Abstracts, Oct. 1999, 2075, 25(2), Abstract 830.12.
Jackson B. Hester et al., J. Med. Chem., 1970, 827–835, 13.
Dong H. Kim, J. Heterocycl. Chem., 1976, 1187–92, 13(6).

Primary Examiner—Brenda Coleman
(74) Attorney, Agent, or Firm—Kimberly R. Hild

(57) ABSTRACT

This invention provides a process for the preparation of 1, 2, 3, 4, 8, 9, 10, 10a-octahydro-7bH-cyclopenta[b][1,4]diazepino[6,7,1-hi]indole derivatives of the general formula:

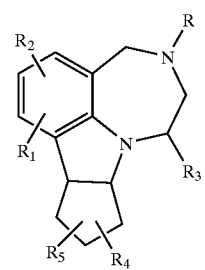

I wherein: R is H, alkyl, cycloalkyl, —$CH_2$-cycloalkyl, acyl, aryl or aroyl; $R_1$, $R_2$, $R_4$ and $R_5$ are H, hydroxy, alkyl, cycloalkyl, alkoxy, halogen, fluorinated alkyl, —CN, —NH—$SO_2$-alkyl, —$SO_2$—NH-alkyl, alkyl amide, amino, alkylamino, dialkylmino, fluorinated alkoxy, acyl, aryl or aroyl; $R_3$ is H, alkyl, cycloalkyl, alkoxy, fluorinated alkyl, alkyl sulfonamide, alkyl amide, amino, alkylamino, dialkylmino, fluorinated alkoxy, acyl, aryl or aroyl; or a pharmaceutically acceptable salt thereof, as well as intermediates for their synthesis.

15 Claims, No Drawings

PROCESS FOR THE PREPARATION OF 1,2,3, 4,8,9,10,10A-OCTAHYDRO-7BH-CYCLOPENTA [B] [1,4] DIAZEPINO- [6,7,1-HI] INDOLE DERIVATIVES

This application claims priority from copending provisional application Ser. No. 60/245,591, filed Nov. 3, 2000, the entire disclosure of which is hereby incorporated by reference.

The present invention provides a process for the preparation of 1, 2, 3, 4, 8, 9, 10, 10a-octahydro-7bH-cyclopenta [b][1,4]diazepino[6,7,1-hi]indole derivatives and salt forms and intermediates thereof, the final compounds being useful as serotonin 5-hydroxytryptamine $2_C$ ($5HT_{2C}$) receptor agonists for the treatment of central nervous system disorders, including obsessive-compulsive disorder, depression, anxiety, generalized anxiety disorder, schizophrenia, panic disorder, migraine, sleep disorders, such as sleep apnea, eating disorders, such as hyperphagia, obesity, epilepsy, and spinal cord injury.

BACKGROUND OF THE INVENTION

Obesity is a medical disorder characterized by an excess of body fat or adipose tissue. Comorbidities associated with obesity are Type II diabetes, cardiovascular disease, hypertension, hyperlipidemia, stroke, osteoarthritis, sleep apnea, gall bladder disease, gout, some cancers, some infertility, and early mortality. As the percentage of obese individuals continues to rise both in the U.S. and abroad, obesity is expected to be a major health risk in the $21^{st}$ Century. The serotonin 5-hydroxytryptamine (5-HT) receptor is a G-protein coupled receptor which is expressed in neurons in many regions of the human central nervous system. [Wilkinson, L. O. and Dourish, C. T. in *Serotonin Receptor Subtypes: Basic and Clinical Aspects* (ed. Peroutka, S. J. ) 147–210 (Wiley-Liss, New York, 1991).] The $5HT_{2c}$ receptor (formerly called the $5HT_{1c}$ receptor) is a prominent subtype of the serotonin receptor found in the central nervous system of both rats and humans. It is expressed widely in both cortical and subcortical regions. [Julius, D. MacDermott, A. B., Axel, R. Jessell, T. M. *Science* 241:558–564 (1988).] Studies in several animal species and in humans have shown that the non-selective $5HT_{2C}$ receptor agonist, meta-chlorophenylpiperazine (MCPP) decreases food intake. [Cowen, P. J., Clifford, E. M., Williams, C., Walsh, A. E. S., Fairburn, C. G. *Nature* 376: 557 (1995).] Tecott, et al have demonstrated that transgenic mice lacking the $5HT_{2C}$ receptor eat more and are heavier than Wild Type mice. [Tecott, L. H., Sun, L. M., Akana, S. F., Strack, A. M., Lowenstein, D. H., Dallman, M. F., Jullus, D. *Nature* 374: 542–546 (1995).] Compounds of this invention are $5HT_{2C}$ receptor subtype selective agonists which are selective over other monoamine receptors, causes a reduction in food intake and result in a reduction in weight gain. Other therapeutic indications for $5HT_{2C}$ agonists are obsessive compulsive disorder, depression, panic disorder, schizophrenia, sleep disorders, eating disorders, and epilepsy.

The non-selective $5\text{-HT}_{2c}$ agonist, meta-chlorophenylpiperazine (m-CPP), has been shown to block conditioned avoidance responding (CAR) in the rat, an activity usually associated with antipsychotic activity in man [Martin, Gregory E.; Elgin, Jr., Robert J.; Mathiasen, Joanne R.; Davis, Coralie B.; Kesslick, James M.; Baldy, William J.; Shank, Richard P.; DiStefano, Deena L.; Fedde, Cynthia L.; Scott, Malcolm K. *J. Med. Chem.* 1989, 32, 1052–1056]. More recently, additional data suggests that $5\text{-HT}_{2c}$ agonism may produce an antipsychotic-like effect in the CAR model [Browning, J. L.; Young, K. A.; Hicks, P. B. Presented at the $29^{th}$ Annual Meeting of the Society for Neuroscience, Miami Beach, Fla., October 1999, Abstract 830.12].

U.S. Pat. No. 3,914,250 (Oct. 21, 1975) describes 1,4-diazepino[6,5,4-jk]carbazoles as anticonvulsant agents.

Pyrrolo[3,2,1-jk][1,4]benzodiazepines and 4,5-dihydropyrrolo[3,2,1-jk][1,4]-benzodiazepines have been described by Hester et al. (*J. Med. Chem.* 1970, 13, 827–835) to have central nervous system activity.

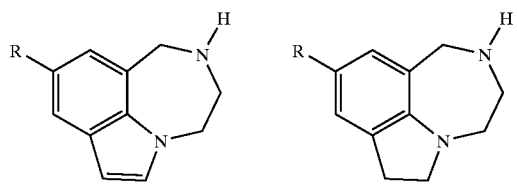

In 1975, Dong H. Kim described 1,4-diazepino[6,5,4-jk] carbazoles (U.S. Pat. No. 3,914,250) and their utility as anticonvulsants.

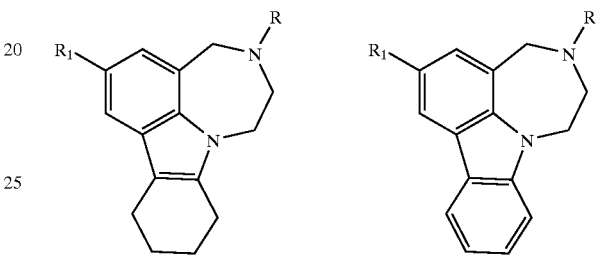

DESCRIPTION OF THE INVENTION

The present invention provides a process for the preparation of 1, 2, 3, 4, 8, 9, 10, 10a-octahydro-7bH-cyclopenta [b][1,4]diazepino[6,7,1-hi]indole derivatives of the general formula:

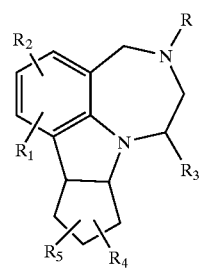

I wherein:
R is hydrogen, alkyl of 1–6 carbon atoms, cycloalkyl of from 3 to 7 carbon atoms, —CH₂-cycloalkyl of from 3 to 7 carbon atoms, acyl of 2–7 carbon atoms, aryl or aroyl;

$R_1$, $R_2$, $R_4$ and $R_5$ are each independently, hydrogen, hydroxy, alkyl of 1–6 carbon atoms, cycloalkyl, alkoxy of 1–6 carbon atoms, halogen, fluorinated alkyl of from 1 to 6 carbon atoms, —CN, —NH—SO₂-alkyl of 1–6 carbon atoms, —SO₂—NH-alkyl of 1–6 carbon atoms, alkyl amide of 1–6 carbon atoms, amino, alkylamino of 1–6 carbon atoms, dialkylmino of 1–6 carbon atoms per alkyl moiety, fluorinated alkoxy of 1–6 carbon atoms, acyl of 2–7 carbon atoms, aryl or aroyl;

$R_3$ is hydrogen, alkyl of 1–6 carbon atoms, cycloalkyl, alkoxy of 1–6 carbon atoms, fluorinated alkyl of from 1 to 6 carbon atoms, alkyl sulfonamide of 1–6 carbon atoms, alkyl amide of 1–6 carbon atoms, amino, alkylamino of 1–6 carbon atoms, dialkylmino of 1–6 carbon atoms per alkyl moiety, fluorinated alkoxy of 1–6 carbon atoms, acyl of 2–7 carbon atoms, aryl or aroyl;

or a pharmaceutically acceptable salt thereof.

In the definitions herein, the fluorinated alkyl and fluorinated alkoxy groups indicate the specified alkyl or alkoxy groups having any amount of fluorine substitution including, but not limited to, groups such as —$CHF_2$, —$CF_3$, —$C_2F_5$, —$OCF_3$, etc.

The compounds prepared by the process of this invention may contain an asymmetric carbon atom and some of the compounds of this invention may contain one or more asymmetric centers and may thus give rise to optical isomers and diastereoisomers. While shown without respect to stereochemistry in Formula I, the present invention includes such optical isomers and diastereoisomers; as well as the racemic and resolved, enantiomerically pure R and S stereoisomers; as well as other mixtures of the R and S stereoisomers and pharmaceutically acceptable salts thereof.

The term "alkyl" includes both straight- and branched-chain saturated aliphatic hydrocarbon groups. The term "aroyl" is defined as an aryl ketone, where aryl is defined as an aromatic system of 6–14 carbon atoms, which may be a single ring or multiple aromatic rings fused or linked together as such that at least one part of the fused or linked rings forms the conjugated aromatic system. Preferred aryl groups include phenyl, naphthyl, biphenyl, anthryl, tetrahydronaphthyl, phenanthryl groups. Halogen is defined as F, Cl, Br and I.

Subsets of the compounds above which may be prepared by the processes described herein include those in which each of R, $R_1$, $R_2$, $R_3$, $R_4$ and $R_5$ are hydrogen. Another group of compounds of this invention include those in which $R_1$ and $R_3$ are hydrogen and R, $R_2$, $R_4$ and $R_5$ are as defined above. In another group, $R_1$, $R_3$ and $R_5$ are hydrogen and R, $R_2$ and $R_4$ are as defined above. A further group of this invention comprises those compounds in which R, $R_1$, $R_2$, $R_3$, and $R_4$ are hydrogen and $R_5$ is as defined above.

It is known that compounds possessing basic nitrogen can complex with many different acids (both protic and non-protic). Each process of this invention is understood to also include an optional additional step of preparing a pharmaceutically acceptable salt form of the compounds described herein formed from the addition reaction with either pharmaceutically acceptable inorganic or organic acids. Inorganic acids such as hydrochloric acid, hydrobromic acid, hydroiodic acid, sulfuric acid, phosphoric acid, nitric acid may be used in these salt forming steps, as well as pharmaceutically acceptable organic acids including, but not limited to, acetic acid, propionic acid, citric acid, maleic acid, malic acid, tartaric acid, phthalic acid, succinic acid, methanesulfonic acid, toluenesulfonic acid, napthalenesulfonic acid, camphorsulfonic acid, and benzenesulfonic acid.

Preferred compounds of this invention are those in which R is hydrogen.

A process of this invention provides a method for preparing compounds of the formula:

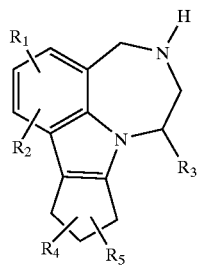

wherein R, $R_1$, $R_2$, $R_3$, $R_4$ and $R_5$ are in each appearance as stated above, the process comprising the steps of:

a) treating a cyclopentaindole methylamine of the formula:

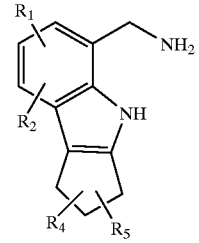

with an acylating agent of the formula:

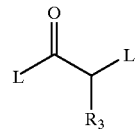

wherein L represents a leaving group as known in the art, such as a halogen, preferably Br, Cl or I, to produce a acylated compound of the formula:

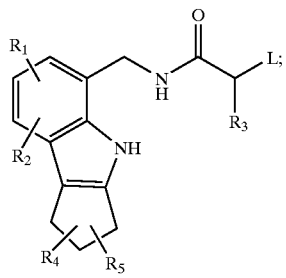

b) cyclizing the acylated compound of step a) to produce an optionally substituted Diazabenzo[cd]cyclopenta[a]azulen-6-one compound of the formula:

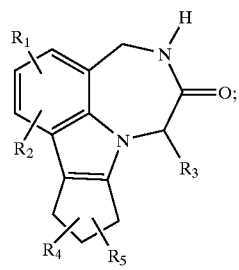

which may be accomplished by treating the acylated compound of step a) with a suitable base in the presence of a polar solvent; and c) treating the Diazabenzo[cd]cyclopenta[a]azulen-6-one compound of step b) with a reducing agent to produce an optionally substituted Diazabenzo[cd]cyclopenta[a]azulene compound of the formula:

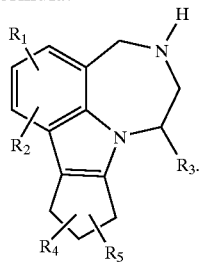

This process further comprises the optional step of treating the Diazabenzo[cd]cyclopenta[a]azulene product of the process above with an alkylating agent to provide a compound of the formula:

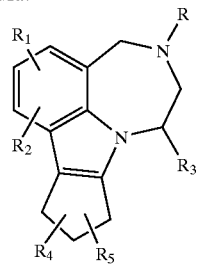

wherein R is an alkyl of 1–6 carbon atoms, cycloalkyl of from 3 to 7 carbon atoms, or —CH$_2$-cycloalkyl of from 3 to 7 carbon atoms; and R$_1$, R$_2$, R$_3$ and R$_4$ and R$_5$ are as described above. The invention also further comprises an optional step in which the Diazabenzo[cd]cyclopenta[a]azulene compound of step c), above, is treated with an acylating agent to produce a compound of the formula, above, wherein R is an acyl group of from 2 to 7 carbon atoms.

In related optional further steps, the alkylated and acylated compounds described above of the formula:

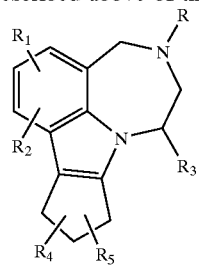

can be treated with a reducing agent to prepare compounds of the formula:

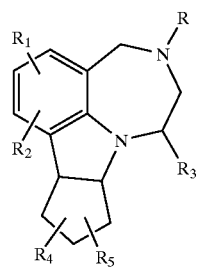

wherein R is, respectively, either an alkyl group of 1–6 carbon atoms, cycloalkyl of from 3 to 7 carbon atoms, —CH$_2$-cycloalkyl of from 3 to 7 carbon atoms, or an acyl group of 2–7 carbon atoms and R$_1$, R$_2$, R$_3$, R$_4$ and R$_5$ are as defined above.

The process of this invention also optionally comprises a further step of reducing the optionally substituted Diazabenzo[cd]cyclopenta[a]azulene compound of step c), above, to provide a compound of the formula:

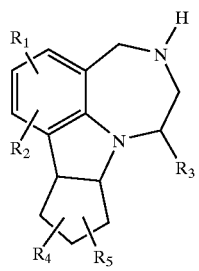

wherein R$_1$, R$_2$, R$_3$ and R$_4$ and R$_5$ are as described above. The reduction can be accomplished by treatment with conventional reducing agents.

A further optional step of this process comprises alkylating the reduced compound above to provide an alkylated compound of the formula:

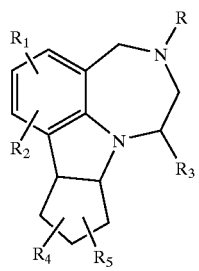

wherein R is an alkyl of 1–6 carbon atoms, cycloalkyl of from 3 to 7 carbon atoms, or —CH$_2$-cycloalkyl of from 3 to 7 carbon atoms; and R$_1$, R$_2$, R$_3$ and R$_4$ and R$_5$ are as described above. The invention also further comprises an optional step in which the reduced compound, above, is treated with an acylating agent to produce a compound of the formula, above, wherein R is an acyl group of from 2 to 7 carbon atoms.

It will be understood that the beginning optionally substituted cyclopentaindole methylamine compounds of step a), above, may be prepared by a number of synthetic methods known in the art. Additional steps within the scope of this invention for the preparation of this compound include:

a) allowing an optionally substituted 2-halophenylhydrazine compound of the formula:

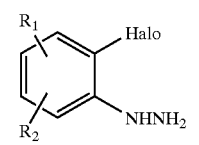

wherein Halo represents a halogen, preferably Br or I, and R$_1$ and R$_2$ are as defined above, to react with an optionally substituted cyclopentanone compound of the formula:

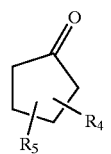

wherein $R_4$ and $R_5$ are as defined above, to produce a 5-halo-cyclopenta[b]indole compound of the formula:

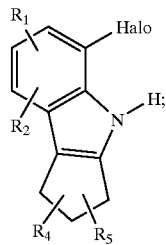

b) converting the 5-halo-cyclopenta[b]indole compound of step a) to an optionally substituted cyclopenta[b]indole aldehyde of the formula:

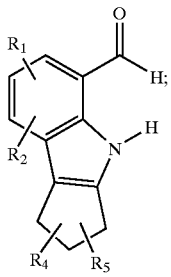

c) converting the optionally substituted cyclopenta[b] indole aldehyde of step b) to a corresponding optionally substituted cyclopenta[b]indole-5-carbaldehyde oxime of the formula:

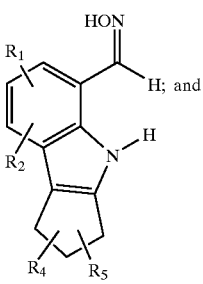

d) treating the optionally substituted cyclopenta[b]indole-5-carbaldehyde oxime of step c) with a reducing agent to provide a cyclopentaindole methylamine of the formula:

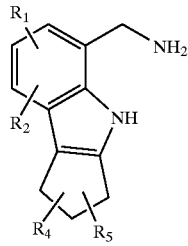

wherein $R_1$, $R_2$, $R_4$ and $R_5$ are as described above.

Scheme I, wherein R, $R_1$, $R_2$, $R_3$ and $R_4$ are as stated above, describes process steps of this invention in additional detail. A 2-bromophenylhydrazine II is allowed to react with a ketone III under standard Fisher-indole conditions. The reaction is carried out in the presence of an acid, such as sulfuric acid, acetic acid, or p-toluenesulfonic acid with or without a solvent, such as water, alkyl alcohol of 1–6 carbon atoms or dimethylforamide (DMF), at a temperature above ambient temperature, such as 30–150° C.

The resulting bromoindole IV is lithiated with reagent such as n-butyl lithium and formylated with formyl transfer agents such as DMF, N-formyl morpholine or ethyl formate in an acceptable solvent such as diethyl ether (Et$_2$O) or methyl t-butyl ether (MTBE) from −78° C. to ambient temperature.

The resulting indole aldehyde V is converted to an indole oxime VI using reagent such as hydroxylamine, N— or O-benzyl protected hydroxylamine in the presence of a suitable base such as pyridine or triethylamine (TEA) in a suitable solvent such as pyridine, water or tetrahydrofuran (THF).

Scheme 1

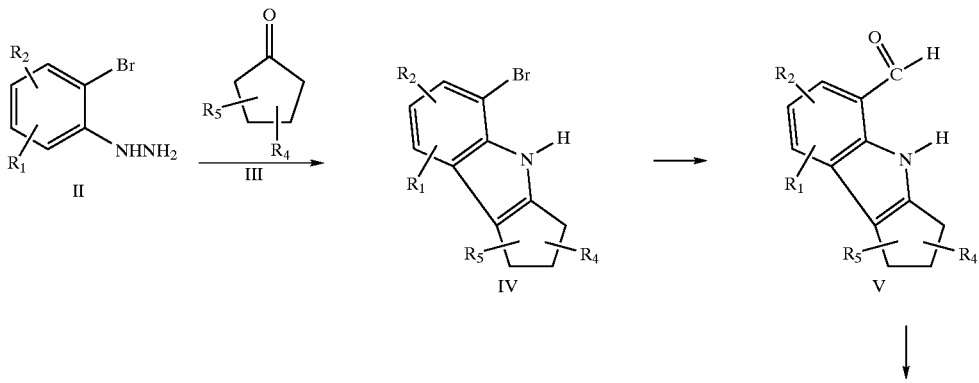

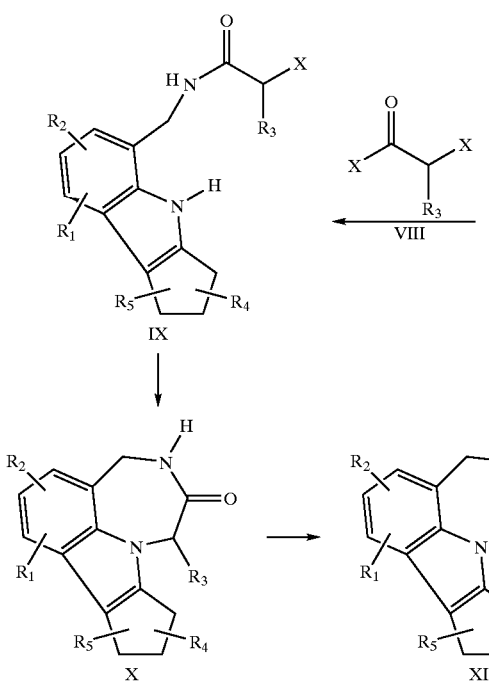
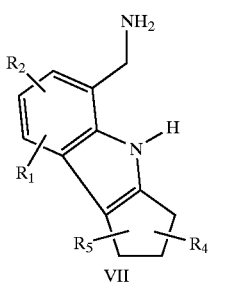
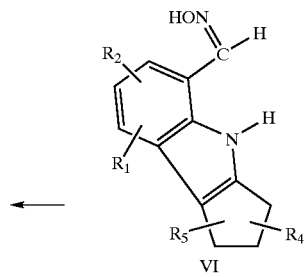

The resulting indole oxime VI can be reduced to indole amine VII using a hydride source such as lithium aluminum hydride (LAH) or by catalytic hydrogenation in the presence of a metal catalyst such as palladium on carbon (Pd/C) or Raney nickel.

The resulting indole amine VII can be acylated with acid halide VIII such as chloroacetyl chloride in the presence of a base such as pyridine or TEA in a suitable solvent such as methylene chloride.

The resulting acyl indole IX can be cyclized to indole amide X in the presence of a suitable base such as sodium hydride (NaH), potassium hydride (KH) or lithium hydride (LiH) in the presence of a polar solvent such as THF, dimethylacetamide (DMA) or DMF.

Indole amide X can be reduced to benzodiazepine indole XI with reagents such as borane, LAH in a suitable solvent such as THF, $Et_2O$ or MTBE. Reduction of benzodiazepine indole XII Reaction of benzodiazepine XII with an alkyl halide of 1–6 carbon atoms such as methyl iodide, or an acyl halide, such as acetyl chloride, or an aroyl chloride, such as benzoyl chloride gives benzodiazepine XIII.

This invention also provides novel compounds which may be used as intermediates in the production of the pharmaceutically useful compounds described herein. These compounds include those of the formulae:

-continued

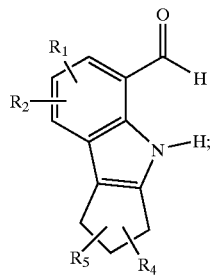

V

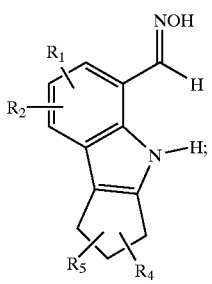

VI

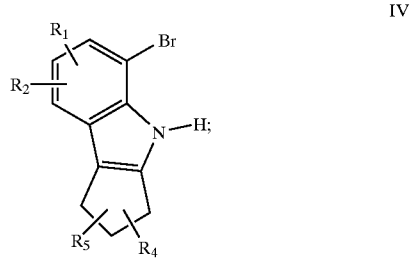

IV

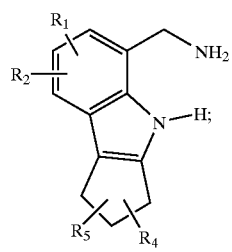

VII

-continued

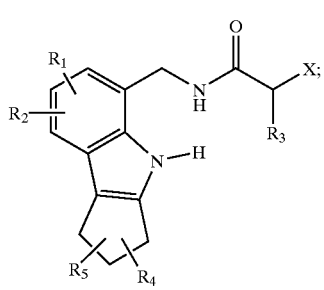

IX

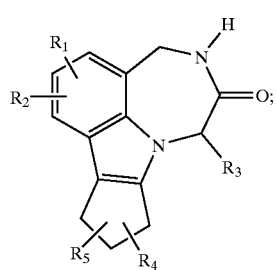

X wherein in each formula $R_1$, $R_2$, $R_3$, $R_4$ and $R_5$ are as defined above and in Formula IX, the moiety X is Cl, Br or I. Subsets of the intermediate compounds of Formulas IV, V, VI, VII, IX and X which may be prepared by the processes described herein include those in which each of $R_1$, $R_2$, $R_3$, $R_4$ and $R_5$ are hydrogen. Another group of compounds of this invention include those in which $R_1$ and $R_3$ are hydrogen and $R_2$, $R_4$ and $R_5$ are as defined above. In another group, $R_1$, $R_3$ and $R_5$ are hydrogen and $R_2$ and $R_4$ are as defined above. A further group of this invention comprises those compounds in which $R_1$, $R_2$, $R_3$, and $R_4$ are hydrogen and $R_5$ is as defined above.

Among the more preferred compounds of these groups are:
5-Bromo-1,2,3,4-tetrahydro-cyclopenta[b]indole;
5-Bromo-3-methyl-1,2,3,4-tetrahydro-cyclopenta[b]indole;
5-Bromo-2-methyl-1,2,3,4-tetrahydro-cyclopenta[b]indole;
5-Bromo-1-methyl-1,2,3,4-tetrahydro-cyclopenta[b]indole;
1,2,3,4-Tetrahydro-cyclopenta[b]indole-5-carbaldehyde;
3-Methyl-1,2,3,4-tetrahydro-cyclopenta[b]indole-5-carbaldehyde;
2-Methyl-1,2,3,4-tetrahydro-cyclopenta[b]indole-5-carbaldehyde;
1-Methyl-1,2,3,4-tetrahydro-cyclopenta[b]indole-5-carbaldehyde;
1,2,3,4-Tetrahydro-cyclopenta[b]indole-5-carbaldehyde oxime;
3-Methyl-1,2,3,4-tetrahydro-cyclopenta[b]indole-5-carbaldehyde oxime;
2-Methyl-1,2,3,4-tetrahydro-cyclopenta[b]indole-5-carbaldehyde oxime;
1-Methyl-1,2,3,4-tetrahydro-cyclopenta[b]indole-5-carbaldehyde oxime;
C-(1,2,3,4-Tetrahydro-cyclopenta[b]indol-5-yl)-methylamine;
C-(3-Methyl-1,2,3,4-tetrahydro-cyclopenta[b]indol-5-yl)-methylamine;
C-(2-Methyl-1,2,3,4-tetrahydro-cyclopenta[b]indol-5-yl)-methylamine;
C-(1-Methyl-1,2,3,4-tetrahydro-cyclopenta[b]indol-5-yl)-methylamine;
2-Chloro-N-(1,2,3,4-tetrahydro-cyclopenta[b]indol-5-ylmethyl)-acetamide;
2-Chloro-N-(3-methyl-1,2,3,4-tetrahydro-cyclopenta[b]indol-5-ylmethyl)-acetamide;
2-Chloro-N-(2-methyl-1,2,3,4-tetrahydro-cyclopenta[b]indol-5-ylmethyl)-acetamide
2-Chloro-N-(1-methyl-1,2,3,4-tetrahydro-cyclopenta[b]indol-5-ylmethyl)-acetamide;
2-Bromo-N-(1,2,3,4-tetrahydro-cyclopenta[b]indol-5-ylmethyl )-acetamide;
2-Bromo-N-(3-methyl-1,2,3,4-tetrahydro-cyclopenta[b]indol-5-ylmethyl)-acetamide;
2-Bromo-N-(2-methyl-1,2,3,4-tetrahydro-cyclopenta[b]indol-5-ylmethyl)-acetamide;
2-Bromo-N-(1-methyl-1,2,3,4-tetrahydro-cyclopenta[b]indol-5-ylmethyl)-acetamide;
2-Iodo-N-(1,2,3,4-tetrahydro-cyclopenta[b]indol-5-ylmethyl)-acetamide;
2-Iodo-N-(3-methyl-1,2,3,4-tetrahydro-cyclopenta[b]indol-5-ylmethyl)-acetamide;
2-Iodo-N-(2-methyl-1,2,3,4-tetrahydro-cyclopenta[b]indol-5-ylmethyl)-acetamide;
2-Iodo-N-(1-methyl-1,2,3,4-tetrahydro-cyclopenta[b]indol-5-ylmethyl)-acetamide;
4,5,9,10-Tetrahydro-8H-5,7a-diaza-benzo[cd]cyclopenta[a]azulen-6-one;
8-Methyl-4,5,9,10-tetrahydro-8H-5,7a-diaza-benzo[cd]cyclopenta[a]azulen-6-one;
9-Methyl-4,5,9,10-tetrahydro-8H-5,7a-diaza-benzo[cd]cyclopenta[a]azulen-6-one; and
10-Methyl-4,5,9,10-tetrahydro-8H-5,7a-diaza-benzo[cd]cyclopenta[a]azulen-6-one.

The acylation steps of this invention are understood to include reactions of the appropriate compound with any acylating agent and reaction conditions known in the art. Useful in these steps are acylating agents include acid halides and esters or anyrides of the appropriate aliphatic carboxylic acid. Useful acid halides include acetyl chloride, propionyl chloride, isobutyryl chloride, benzoyl chloride, etc. Acid anhydrides include acetic anhydride and benzoic anhydride. Similarly, alkylation steps herein are understood to include any relevant alkylating agents and conditions known in the art. These include, but are not limited to the use of alkyl halides, such as methyl iodide, or alkyl tosylates or aldehyde alkylating agents in the presence of an applicable reducing agent.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids. The processes herein will be understood to include an optional additional step of forming a salt form of the products via standard addition reactions with any pharmaceutically acceptable organic or inorganic acid.

A method of resolving the (R,R) enantiomer from racemic mixtures of these compounds comprises the steps of:
a) dissolving about 1 equivalent of the racemic compound mixture of a product of this invention in a solubilizing amount of an alcohol resolving agent at a temperature of from about 50° C. to the reflux temperature for the alcohol, preferably between about 50° C. and 70° C., under an inert atmosphere, to create a resolving solution;
b) treating the resolving solution of step a) with from about 0.1 to about 0.35 equivalents of dibenzoyl-L-tartaric acid, preferably from about 0.15 equivalents to about 0.3 equivalents, more preferably from about 0.23 to about 0.27 equivalents, most preferably about 0.25 equivalents to precipitate the desired (R,R) enantiomer from the resolving solution as the corresponding tartaric acid salt form; and c) separating the desired enantiomer from the resolving solution through conventional means, such as filtration.

It will be understood that this process may be followed by additional steps of filtration and purification to enhance the purity and yield of the desired enantiomer product in question.

In step b) it is preferred that the temperature of the resolving solution be maintained at a temperature at or above about 50° C., preferably nearer to the reflux temperature of the alcohol in question. The alcohol component of step a) may be comprise a single alcohol or a combination of two or more alcohols selected from those known in the art into which the compound in question can be dissolved. Among the preferred alcohols are the commercially available and relatively low boiling alcohols comprising 10 carbon atoms or less including methanol, ethanol, n-propanol, isopropanol, n-butanol, t-butanol, cyclohexanol, etc.

It will also be understood that the (S,S) enantiomer of the racemic mixture mentioned above could then be purified and collected from the remaining resolving solution described above after collection of the (R,R) tartaric acid salt.

An analogous method for resolving the (S,S) enantiomer from the racemic mixtures of compounds of this invention, the method comprising the steps a) through c) listed above, with dibenzoyl-D-tartaric acid being used in place of dibenzoyl-L-tartaric acid in step b). Comparably, the (R,R) enantiomer can be collected and purified by conventional means from the remaining solution after the tartaric acid salt form of the (S,S) enantiomer is precipitated and removed in this analogous method.

The 5HT$_{2C}$ receptor agonists of this invention are useful for the treatment or prevention in mammals, preferably in humans, of disorders involving the central nervous system such as obsessive-compulsive disorder, depression, atypical depression, bipolar disorders, anxiety, generalized anxiety disorder, schizophrenia, psychoses, personality disorders, organic mental disorders, behavioral disorders associated with dementia or age-related conditions, aggressivity, drug and alcohol addiction, social phobias, sexual dysfunction, panic disorder, migraine, sleep disorders, such as sleep apnea, eating disorders, such as hyperphagia, bulimia or anorexia nervosa, obesity, epilepsy, and premenstrual tension.

Methods of utilizing the compounds herein also include treatments or preventative regimens for treatment of central nervous system deficiencies associated with trauma, stroke, neurodegenerative diseases or toxic or infective CNS disorders including, but not limited to, encephalitis or meningitis; or cardiovascular disorders, including thrombosis; gastrointestinal disorders such as malfunction of gastrointestinal motility; and diabetes insipidus. These methods include the improvement or inhibition of further degradation of central nervous system activity during or following the malady or trauma in question. Included in these improvements are maintenance or improvement in motor and motility skills, control, coordination and strength.

The following examples illustrate the present invention in more detail; however, they are not intended to limit its scope in any manner.

EXAMPLE 1

Fisher Indole Synthesis of 5-Bromo-1,2,3,4-Tetrahydrocyclopenta[b]Indole

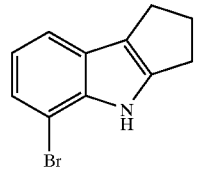

A mixture of 2-bromophenylhydrazine hydrochloride (130 g, 0.582 mol) and cyclopentanone (60 mL, 0.678 mol) in 4% sulfuric acid (1 L) was heated to 98–100° C. for 6 h. This was then allowed to cool to rt overnight. After 12 h, the liquid was decanted leaving a red, gummy solid. (5:1) Hexane:EtOAc (1.5 L) was added to the flask and the mixture was hot filtered. The organic layer was concentrated in vacuo to give a brown oil which solidified upon standing to give 77.4 g (59%) of a brown solid.

R$_f$=0.54 (hexane:EtOAc);

$^1$H NMR (CDCl$_3$) δ 8.12 (d, J=8.6 Hz, 1H), 7.76 (m, 2H), 7.51 (d, J=9 Hz, 1H), 7.20–7.60 (m, 4H), 4.5–4.6 (m, 1H), 4.2–4.4 (m, 3H), 4.1–4.2 (m, 1H), 2.70 (s, 3H), 2.39 (s, 3H);

$^{13}$C NMR (DMSO) δ 144.8, 139.6, 126.4, 123.2, 121.4, 121.0, 118.1, 104.9, 29.0, 26.3, 25.0;

IR (KBr): υ$_{max}$ 3436, 2941, 2856, 1616, 1575, 1463, 1416, 1295, 1210, 1094, 768, 729, 629, 463 cm$^{-1}$.

Analysis for C$_{11}$H$_{10}$BrN: Calculated: C, 55.91; H, 4.24 N 5.93. Found: C, 57.13; H, 4.22; N, 5.97.

EXAMPLE 2

Formylation to 1,2,3,4-Tetrahydrocyclopenta[b]Indole-5-Carbaldehyde

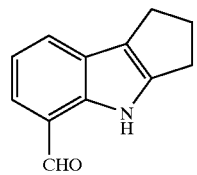

A solution of 5-bromo-1,2,3,4-tetrahydrocyclopenta[b] indole (15.5 g, 65.1 mmol) in MTBE (130 mL) was cooled to 0–5° C. in an ice-bath before n-BuLi in hexanes (2.5 M, 57.5 mL, 144 mmol) was added slowly while keeping the reaction mixture below 20° C. After 30 min, DMF (50.5 mL, 0.652 mmol) was added slowly. Some solid precipitate formed upon addition. This was stirred under these conditions for an additional 1 h then the ice-bath was removed to allowed the reaction mixture to warm to rt. MTBE (130 mL) and water (100 mL) were added. The two layer were separated. The aqueous layer was extracted with MTBE (2×50 mL). The combined organic layers were dried over Na$_2$SO$_4$, filtered and concentrated in vacuo to afford 15.4 g (127%) of crude product as a light brown solid.

R$_f$=0.41 (5:1 hexane:EtOAc);

$^1$H NMR (CDCl$_3$) δ 10.1 (s, 1H), 9.9 (bs, 1H), 7.71 (d, J=7.8 Hz, 1H), 7.52 (d, J=7.4 Hz, 1H), 7.19 (t, J=7.6 Hz, 1H), 2.7–3.0 (m, 4H), 2.4–2.6 (m, 2H);

$^{13}$C NMR (CDCl$_3$) δ 193.7, 146.0, 138.5, 127.1, 125.7, 120.3, 119.7, 118.9, 28.8, 25.7, 24.2; GC/MS 185, 158, 128, 115, 102, 91, 77, 70, 63, 57, 51, 45, 39, 39;

IR (KBr): $\upsilon_{max}$ 3394, 2909, 2862, 2799, 2727, 1668, 1565, 1472, 1352, 1185, 1124, 780, 662 cm$^{-1}$.

EXAMPLE 3

Preparation of 1,2,3,4-Tetrahydrocyclopenta[b] Indole-5-Carbaldehyde Oxime

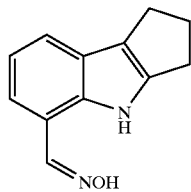

A mixture of 1,2,3,4-tetrahydrocyclopenta[b]indole-5-carbaldehyde (100 mg, 0.54 mmol) and hydroxylamine hydrochloride (60 mg, 0.86 mmol) in (2:1) pyridine:H$_2$O (4.5 mL) was stirred at rt. After 16 h, CHCl$_3$ (25 mL) and H$_2$O (15 mL) were added to the reaction mixture. The two layers were separated. The organic layer was extracted with 1 N HCl (2×10 mL), H$_2$O (10 mL), dried over Na$_2$SO$_4$, filtered and concentrated in vacuo to afford 117 mg (108%) of crude product as a brown oil.

$R_f$=0.50 (20:1 CHCl$_3$:CH$_3$OH);

$^1$H NMR (CDCl$_3$) δ 9.50 (bs, 1H), 8.23 (s, 1H), 7.3–7.5 (m, 1H), 6.8–7.0 (m, 2H), 3.6–2.8 (m, 4H), 2.2–2.5 (m, 2H).

EXAMPLE 4

Oxime Reduction to 1,2,3,4-Tetrahydrocyclopenta [b]Indol-5-ylmethylamine

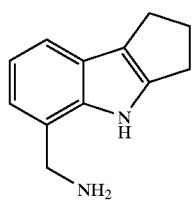

A solution of 1,2,3,4-tetrahydrocyclopenta[b]indole-5-carbaldehyde oxime (1.6 g, 8.1 mmol) in THF (30 mL) was cooled to 0–5° C. in an ice-bath under Ar. LAH (0.93 g, 24.5 mmol) was added in small portions. After 2 h, the ice-bath was removed to warm the reaction mixture to rt over 16 h before a sat'd Na$_2$SO$_4$ solution (1.5 mL) was added dropwise to quench the excess reagent. After 30 min of stirring, solid Na$_2$SO$_4$ and Et$_2$O (30 mL) were added. The suspension was filtered and concentrated in vacuo to give 1.05 g (69%) of the title compound as a yellow solid.

$^1$H NMR (CDCl$_3$) δ 9.3 (bs, 1H), 7.34 (d, J=7.8 Hz, 1H), 6.99 (t, J=7.5 Hz, 1H), 6.89 (d, J=7.1 Hz, 1H), 4.22 (s, 2H), 2.7–3.0 (m, 4H), 2.4–2.6 (m, 2H), 1.6 (bs, 2H);

$^{13}$C NMR (CDCl$_3$) δ 144.0, 140.0, 125.1, 125.2, 119.0, 118.9, 117.4, 45.3, 28.8, 25.9, 24.1; IR (KBr): $\upsilon_{max}$ 3417, 3352, 3289, 3055, 2897, 2849, 1615, 1582, 1419, 1325, 1229, 1129, 1000, 897, 741 cm$^{-1}$.

Analysis for C$_{12}$H$_{14}$N$_2$: Calculated: C, 77.42; H, 7.53; N, 15.05; Found: C, 74.60; H, 7.31; N, 13.52

EXAMPLE 5

One-Pot Reductive Amination to 1,2,3,4-Tetrahydrocyclopenta[b]Indol-5-ylmethylamine A mixture of 1,2,3,4-tetrahydrocyclopenta[b]indole-5-carbaldehyde (578 mg, 3.12 mmol), hydroxylamine hydrochloride (238 mg, 3.42 mmol) and pyridine (3 mL) in THF (15 mL) was stirred at rt. After 5.5 h, the reaction mixture was cooled to 0–5° C. in an ice-bath before LAH power (474 mg, 12.5 mmol) was added portionwise. The reaction mixture was then warmed to rt overnight before a sat'd Na$_2$SO$_4$ solution (1 mL) was added dropwise to quench the excess reagent. After 30 min of stirring, solid Na$_2$SO$_4$ and Et$_2$O (30 mL) were added. The suspension was filtered and concentrated in vacuo to give 338 mg (58%) of the title compound as a yellow solid.

EXAMPLE 6

Acylation to 2-Chloro-N-(1,2,3,4-Tetrahydrocyclopenta[b]Indol-5-ylmethyl) Acetamide

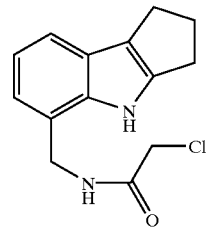

A solution of 1,2,3,4-tetrahydrocyclopenta[b]indol-5-ylmethylamine (100 mg, 0.538 mmol) and pyridine (0.1 mL, 1.23 mmol) in CH$_2$Cl$_2$ (2 mL) was cooled to 0–5° C. in an ice-bath under Ar before chloroacetyl chloride (62 µL, 0.59 mmol) was added. After 1 h, the ice-bath was removed to allow the reaction to warm to rt. After an additional 12 h, H$_2$O (3 mL) and CHCl$_3$ (3 mL) were added. The two layers were separated. The organic layer was dried over Na$_2$SO$_4$, filtered and concentrated in vacuo. Purification on SiO$_2$, eluted with (40:1) CHCl$_3$:CH$_3$OH gave 80 mg (57%) of the title compound as a yellow solid.

$R_f$=0.52 (40:1 CHCl$_3$:CH$_3$OH);

$^1$H NMR (CDCl$_3$) δ 9.37 (bs, 1H), 7.41 (d, J=7.5 Hz, 1H), 7.16 (bs, 1H), 7.01 (t, J=7.3 Hz, 1H), 6.96 (d, J=7.8 Hz, 1H), 4.68 (d, J=6.8 Hz, 2H), 4.08 (s, 2H), 2.7–3.0 (m, 4H), 2.4–2.6 (m, 2H);

$^{13}$C NMR (CDCl$_3$) δ 167.6, 145.0, 139.8, 125.4, 121.4, 121.2, 120.9, 120.2, 119.4, 43.0, 41.9, 29.2, 26.4, 24.8.

EXAMPLE 7

Seven-Membered Ring Closure to 3,4,9,10-Tetrahydro-8H-Cyclopenta[b][1,4]Diazepino[6,7,1-hi]Indol-2(1H)-One

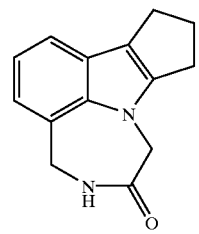

To a suspension of NaH (124 mg, 3.10 mmol) in DMF (3 mL), 2-chloro-N-(1,2,3,4-tetrahydrocyclopenta[b]indol-5-ylmethyl)acetamide (135 mg, 0.515 mmol) in DMF (3 mL) was added at rt under Ar. After 16 h, H$_2$O (2 mL) was added to quench the excess reagent, H$_2$ evolved upon addition. After an additional 30 min, CHCl$_3$ (20 mL) and H$_2$O (10 mL) were added. The two layers were separated. The aqueous layer was extracted with CHCl$_3$ (10 mL). The combined organic layers were dried over Na$_2$SO$_4$, filtered and concentrated in vacuo. Purification on SiO$_2$, eluted with (30:1) CHCl$_3$:CH$_3$OH gave 67 mg (58%) of the title compound as a brown solid.

R$_f$=0.53 (20:1 CHCl$_3$:CH$_3$OH);

$^1$H NMR (CDCl$_3$) δ 7.99 (bs, 1H), 7.33 (d, J=7.8 Hz, 1H), 6.95 (t, J=7.2 Hz, 1H), 6.75 (d, J=7.2 Hz, 1H), 4.87 (s, 2H), 4.56 (d, J=6.2 Hz, 2H), 2.7–3.0 (m, 4H), 2.4–2.6 (m, 2H);

$^{13}$C NMR (CDCl$_3$) δ 170.0, 146.6, 139.4, 125.1, 121.4, 119.6, 119.2, 118.8, 118.5, 51.3, 44.5, 28.7, 25.1, 25.0.

EXAMPLE 8

Reduction to 3,4,9,10-Tetrahydro-8H-Cyclopenta[b][1,4]Diazepino[6,7,1-hi]Indole

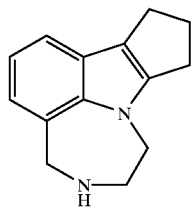

To a suspension of 3,4,9,10-tetrahydro-8H-cyclopenta[b][1,4]diazepino[6,7,1-hi]indol-2(1H)-one (67 mg, 0.30 mmol) in Et$_2$O (7 mL), LAH power (28 mg, 0.74 mmol) was added slowly at rt under Ar. After 16 h, additional Et$_2$O (5 mL) was added followed by dropwise addition of a sat'd Na$_2$SO$_4$ solution (0.1 mL). H$_2$ gas evolved upon addition. Additional Et$_2$O (8 mL) was added, dried over Na$_2$SO$_4$, filtered and concentrated in vacuo to give 44 mg (70%) of the title compound as a yellow syrup.

$^1$H NMR (CDCl$_3$) δ 7.30 (d, J=7.7 Hz, 1H), 7.0 (t, J=7.5 Hz, 1H), 6.8 (d, J=7.1 Hz, 1H), 5.29 (s, 2H), 3.99 (t, J=5.1 Hz, 2H), 3.33 (t, J=5.0 Hz, 2H), 2.8–2.9 (m, 4H), 2.4–2.6 (m, 2H).

EXAMPLE 9

Preparation of 1,2,3,4,8,9,10,10a-Octahydro-7bH-Cyclopenta[b][1,4]-Diazepino[6,7,1-hi]Indole

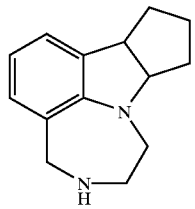

To a solution of 3,4,9,10-tetrahydro-8H-cyclopenta[b][1,4]diazepino[6,7,1-hi]indole (61 mg, 0.29 mmol) in TFA (2 mL) being cooled in an ice-bath, BH$_3$.THF (0.7 mL, 0.7 mmol, 1 M THF) was added slowly under Ar. After 4 h, the reaction mixture was concentrated in vacuo then CHCl$_3$ (3 mL) and 1 N HCl (3 mL) were added. The mixture was stirred for 1 h before separating the two layers. The aqueous layer was basified to pH 13–14 with 5 N NaOH then extracted with CHCl$_3$ (3×3 mL). The combined organic layers was dried over Na$_2$SO$_4$, filtered and concentrated in vacuo to give 36 mg (58%) of the title compound as a thin white film.

$^1$H NMR (DMSO-d$_6$) δ 6.86 (d, J=7.2 Hz, 1H), 6.74 (d, J=7.4 Hz, 1H), 6.53 (t, J=7.3 Hz, 1H), 3.88 (m, 1H), 3.81, 3.47 (ABq, J$_{AB}$=15.1 Hz, 2H), 3.73 (m, 1H), 3.08 (m, 2H), 2.55–2.80 (m, 2H), 2.15 (bs, 1H), 1.3–2.0 (m, 6H).

What is claimed is:

1. A process for preparing compounds of the formula:

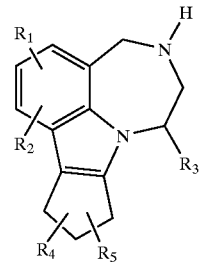

wherein:

R$_1$, R$_2$, R$_4$ and R$_5$ are each independently, hydrogen, hydroxy, alkyl of 1–6 carbon atoms, cycloalkyl, alkoxy of 1–6 carbon atoms, halogen, fluorinated alkyl of from 1 to 6 carbon atoms, —CN, —NH—SO$_2$-alkyl of 1–6 carbon atoms, —SO$_2$—NH-alkyl of 1–6 carbon atoms, alkyl amide of 1–6 carbon atoms, amino, alkylamino of 1–6 carbon atoms, dialkylmino of 1–6 carbon atoms per alkyl moiety, fluorinated alkoxy of 1–6 carbon atoms, acyl of 2–7 carbon atoms, aryl or aroyl;

R$_3$ is hydrogen, alkyl of 1–6 carbon atoms, cycloalkyl, alkoxy of 1–6 carbon atoms, fluorinated alkyl of from 1 to 6 carbon atoms, alkyl sulfonamide of 1–6 carbon atoms, alkyl amide of 1–6 carbon atoms, amino, alkylamino of 1–6 carbon atoms, dialkylmino of 1–6 carbon atoms per alkyl moiety, fluorinated alkoxy of 1–6 carbon atoms, acyl of 2–7 carbon atoms, aryl or aroyl; the process comprising the steps of:

a) acylating a cyclopentaindole methylamine of the formula:

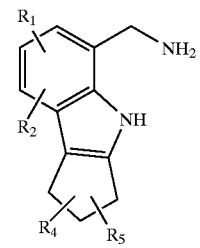

with an acylating agent of the formula:

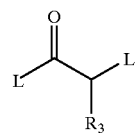

wherein $R_1$, $R_2$, $R_3$, $R_4$ and $R_5$ are as defined above and L represents a leaving group to produce an acylated compound of the formula:

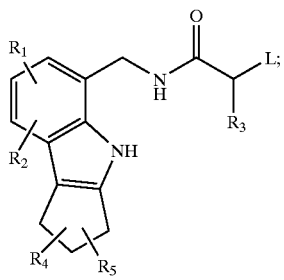

b) cyclizing the acylated compound of step a) to produce an optionally substituted diazabenzo[cd]cyclopenta[a]azulen-6-one compound of the formula:

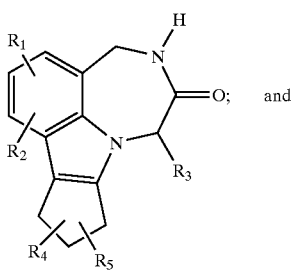

c) reducing the diazabenzo[cd]cyclopenta[a]azulen-6-one compound of step b) to produce an optionally substituted diazabenzo[cd]cyclopenta[a]azulene compound of the formula:

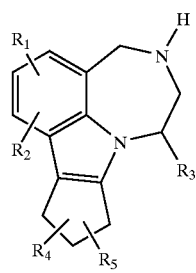

2. The process of claim 1 further comprising the step of treating the diazabenzo[cd]cyclopenta[a]azulene compound of step c) of claim 1 with an alkylating agent to provide an alkylated compound of the formula:

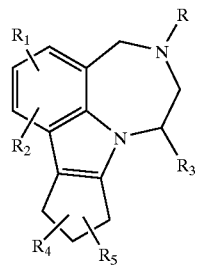

wherein R is an alkyl group of 1–6 carbon atoms, cycloalkyl of from 3 to 7 carbon atoms, or —CH$_2$-cycloalkyl of from 3 to 7 carbon atoms; and $R_1$, $R_2$, $R_3$ and $R_4$ and $R_5$ are as described in claim 1.

3. The process of claim 2 further comprising the step of treating the alkylated compound of claim 2 with a reducing agent to produce a compound of the formula:

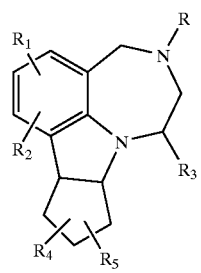

wherein R, $R_1$, $R_2$, $R_3$ and $R_4$ and $R_5$ are as described in claim 2.

4. The process of claim 1 further comprising the step of treating the diazabenzo[cd]cyclopenta[a]azulene compound of step c) of claim 1, with an acylating agent to produce an acylated compound of the formula:

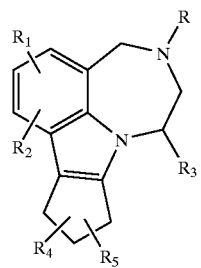

wherein R is an acyl group of from 2 to 7 carbon atoms and $R_1$, $R_2$, $R_3$ and $R_4$ and $R_5$ are as described in claim 1.

5. The process of claim 4 further comprising the step of treating the acylated compound of claim 4 with a reducing agent to produce a compound of the formula:

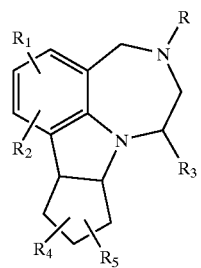

wherein R, $R_1$, $R_2$, $R_3$ and $R_4$ and $R_5$ are as described in claim 4.

6. The process of claim 1 comprising a further step of treating the optionally substituted diazabenzo[cd]cyclopenta[a]azulene compound of step c) of claim 1 with a reducing agent to provide a reduced compound of the formula:

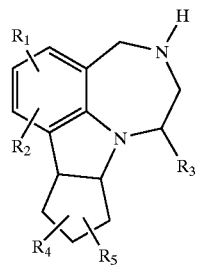

wherein $R_1$, $R_2$, $R_3$ and $R_4$ and $R_5$ are as described in claim 1.

7. The process of claim 6 further comprising the step of treating the reduced compound of claim 6 with an alkylating agent to provide an alkylated compound of the formula:

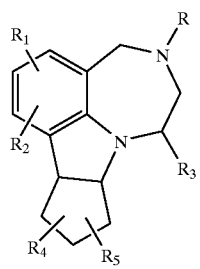

wherein R is an alkyl of 1–6 carbon atoms, cycloalkyl of from 3 to 7 carbon atoms, or —$CH_2$-cycloalkyl of from 3 to 7 carbon atoms; and $R_1$, $R_2$, $R_3$ and $R_4$ and $R_5$ are as described in claim 6.

8. The process of claim 6 further comprising the step of treating the reduced compound of claim 6 with an acylating agent to provide an acylated compound of the formula:

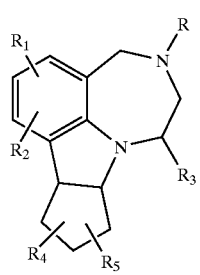

wherein R is an acyl group of from 2 to 7 carbon atoms; and $R_1$, $R_2$, $R_3$ and $R_4$ and $R_5$ are as described in claim 6.

9. The process of claim 1 further comprising the step of treating the compound of the formula:

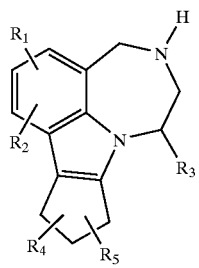

wherein $R_1$, $R_2$, $R_3$, $R_4$ and $R_5$ are as defined in claim 1, with a pharmaceutically acceptable inorganic or organic acid to form a pharmaceutically acceptable salt of the compound.

10. The process of claim 9 wherein the pharmaceutically acceptable inorganic or organic acid is selected from the group consisting of hydrochloric acid, hydrobromic acid, hydroiodic acid, sulfuric acid, phosphoric acid, nitric acid, acetic acid, propionic acid, citric acid, maleic acid, malic acid, tartaric acid, phthalic acid, succinic acid, methanesulfonic acid, toluenesulfonic acid, napthalenesulfonic acid, camphorsulfonic acid, and benzenesulfonic acid.

11. The process of claim 1 wherein each of $R_1$, $R_2$, $R_3$, $R_4$ and $R_5$ are hydrogen.

12. The process of claim 1 wherein $R_1$ and $R_3$ are hydrogen and $R_2$, $R_4$ and $R_5$ are as defined in claim 1.

13. The process of claim 1 wherein $R_1$, $R_3$ and $R_5$ are hydrogen and $R_2$ and $R_4$ are defined as in claim 1.

14. The process of claim 1 wherein $R_1$, $R_2$, $R_3$, and $R_4$ are hydrogen and $R_5$ is as defined in claim 1.

15. The process of claim 1 wherein the cyclopentaindole methylamine is formed by the steps comprising:

i) allowing an optionally substituted 2-halophenylhydrazine compound of the formula:

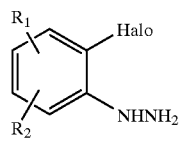

to react with an optionally substituted cyclopentanone compound of the formula:

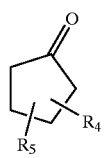

to produce a 5-halo-cyclopenta[b]indole compound of the formula:

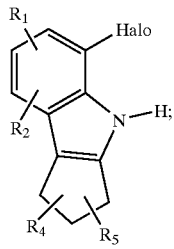

wherein $R_1$, $R_2$, $R_4$ and $R_5$ are defined as in claim 1 and Halo is a halogen atom;

ii) converting the 5-halo-cyclopenta[b]indole compound of step i) to an optionally substituted cyclopenta[b]indole aldehyde of the formula:

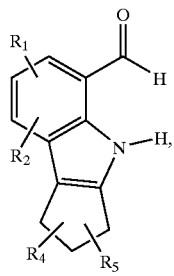

iii) converting the optionally substituted cyclopenta[b]indole aldehyde of step ii) to a corresponding optionally substituted cyclopenta[b]indole-5-carbaldehyde oxime of the formula:

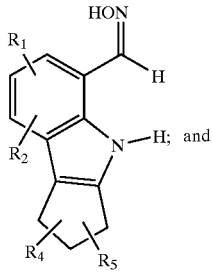

iv) treating the optionally substituted cyclopenta[b]indole-5-carbaldehyde oxime of step iii) with a reducing agent to provide a cyclopentaindole methylamine of the formula:

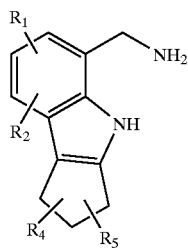

wherein $R_1$, $R_2$, $R_4$ and $R_5$ are defined as in claim 1.

* * * * *